United States Patent
Burzynski

(10) Patent No.: US 6,987,131 B1
(45) Date of Patent: Jan. 17, 2006

(54) PHENYLACETIC ACID COMPOSITIONS FOR TREATING OR PREVENTING HYPERCHOLESTEROLEMIA

(76) Inventor: Stanislaw R. Burzynski, 20 W. Rivercrest, Houston, TX (US) 77042

( * ) Notice: Subject to any disclaimer, the term of this patent is extended or adjusted under 35 U.S.C. 154(b) by 879 days.

(21) Appl. No.: 09/603,320

(22) Filed: Jun. 26, 2000

(51) Int. Cl.
*A61K 31/195* (2006.01)
(52) U.S. Cl. .................................... 514/563
(58) Field of Classification Search ............. 514/563
See application file for complete search history.

(56) References Cited

U.S. PATENT DOCUMENTS

| | | | |
|---|---|---|---|
| 4,470,970 A | 9/1984 | Burzynski | 424/177 |
| 5,153,226 A | 10/1992 | Chucholowski et al. | 514/617 |
| 5,238,947 A * | 8/1993 | Hendry et al. | |
| 5,352,687 A | 10/1994 | Müller et al. | 514/341 |
| 5,480,910 A | 1/1996 | Holloway et al. | 514/567 |
| 5,521,206 A | 5/1996 | Müller et al. | 514/400 |
| 5,712,307 A | 1/1998 | Samid | 514/538 |

\* cited by examiner

*Primary Examiner*—San-Ming Hui
(74) *Attorney, Agent, or Firm*—Howrey LLP

(57) ABSTRACT

Pharmaceutical compositions are disclosed comprising one or more compounds selected from the group consisting of phenylacetylglutamine, phenylacetylisoglutamine, and phenylacetic acid, in addition to pharmaceutically-acceptable salts, analogs, and precursors thereof, and optionally also isoglutamine, with a pharmaceutically-acceptable carrier, diluent, or excipient, useful in the treatment or prevention of hypercholesterolemia and hypertriglyceridemia. Also disclosed are methods for treating or preventing hypercholesterolemia and hypertriglyceridemia using the pharmaceutical compositions.

8 Claims, No Drawings

PHENYLACETIC ACID COMPOSITIONS FOR TREATING OR PREVENTING HYPERCHOLESTEROLEMIA

BACKGROUND OF THE INVENTION

1. Field of the Invention

The present invention relates generally to the field of pharmaceutical chemistry. More particularly, it concerns the use of an effective amount of phenylacetic acid, phenylacetylglutamine, or phenylacetylisoglutamine, or pharmaceutically acceptable salts thereof, pharmaceutically acceptable precursors thereof, or pharmaceutically acceptable analogs thereof, singly or in any combination, and optionally including isoglutamine, in the treatment and prevention of hypercholesterolemia and hypertriglyceridemia.

2. Description of Related Art

In the United States, roughly 500,000 people die from coronary heart disease and 750,000 suffer heart attacks every year. Thousands more also die of stroke. A major cause of heart disease, heart attack, and stroke is atherosclerosis. Atherosclerosis is the growth of lesions on the walls of the aorta and other arteries, and its asymptomatic early stages are ubiquitous in populations with high-caloric, fat-rich diets such as are common in the United States and Europe. In its advanced stages, atherosclerotic lesions, commonly termed plaques, lead to constriction of the arterial lumen, resulting in impaired oxygen flow to the heart (angina) and the potential for thrombosis (blockage of blood flow by the presence of a clot), which may cause a heart attack or stroke.

Atherosclerotic lesions originate in the lining (intima) or middle layer (media) of the aorta and other arteries, as a focal overgrowth of smooth muscle cells. Recent investigations have uncovered evidence that a lesion may be a monoclonal overgrowth of smooth muscle cells. In other words, a lesion may correspond to a benign smooth muscle tumor. Although detailed understanding of this phenomenon remains the subject of inquiry, it has recently been postulated that smooth muscle cell proliferation may be caused, at least in part, by inactivation of the tumor suppressor gene p53.

Currently, factors that increase the risk of atherosclerosis are fairly well known. These factors include diets high in saturated fats and cholesterol, smoking, obesity, and conditions such as diabetes. Elimination or minimization of these risk factors has value in slowing the advancement of atherosclerosis. Of these, minimizing cholesterol intake, especially LDL cholesterol, has been highly publicized in recent years. It has been reported that both native and oxidized LDL cholesterol stimulate DNA synthesis in cultured human smooth muscle cells (Stiko-Rahm et al., *Arterioscler. Thromb.* 12, 9: 1099–1109 (1992)).

Several observations complicate the minimization of cholesterol intake. One is patient compliance with dietary restrictions. A regimen of pharmaceutical treatment to lower cholesterol levels may be more readily complied with than would a change in lifelong eating habits. Another observation is that hypercholesterolemia can occur due to non-dietary conditions, for example, essential hypercholesterolemia, a familial trait characterized by a genetically-determined low level of LDL receptors, and liver disorders which impair excretion of cholesterol in the bile, for example, jaundice. These patients would benefit from a pharmaceutical treatment to lower cholesterol levels.

Triglycerides are the form in which fat is stored by the body. High triglyceride levels have been observed in patients with hypercholesterolemia and other risk factors for heart disease. Although it is not known if hypertriglyceridemia leads to heart disease, a pharmaceutical treatment to lower triglyceride levels would be of benefit to patients.

It has been known for some time that compounds such as 3-phenylacetylamino-2,6-piperidinedione and its hydrolysis products, such as phenylacetic acid, and salts, precursors, and analogs thereof (together, "3-phenylacetylamino-2,6-piperidinedione and its derivatives"), can block the formation of iso-pentenylpyrophosphate from 5-pyrophosphomevalonate, a reaction in the pathway of cholesterol biosynthesis; as a result, these compounds may lower serum cholesterol levels. Therefore, it was desirable to determine which, if any, of ~3-phenylacetylamino-2,6-piperidinedione and its derivatives can lower serum cholesterol levels, and thus can form the basis of a pharmaceutical composition useful in treating or preventing hypercholesterolemia. Derivatives of 3-phenylacetylamino-2,6-piperidinedione that exhibit such activity are disclosed herein.

SUMMARY OF THE INVENTION

In one aspect, the present invention includes a method for the treatment or prevention of hypercholesterolemia comprising the step of administering to a patient a pharmaceutical composition comprising a therapeutically-effective amount of a compound of Formula I:

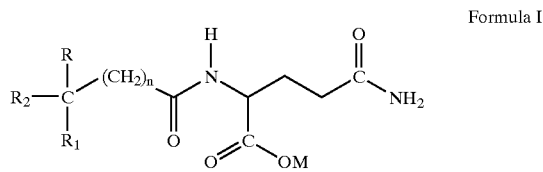

Formula I wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, sodium, potassium, ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5. Preferably, M is hydrogen or sodium; n is 0; R is selected from the group consisting of H and $C_3H_7$; $R_1$ is selected from the group consisting of H, $CH_3$, $CH_3$—O—, $C_2H_5$, and $C_3H_7$; and $R_2$ is an aryl ($C_{6-12}$) or a substituted aryl selected from the group consisting of Formula II:

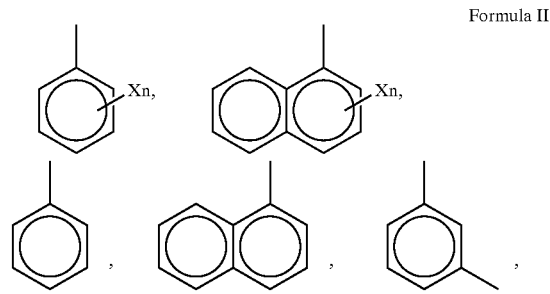

Formula II

-continued

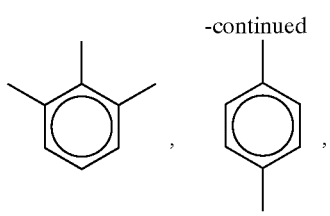

wherein X is a halogen, lower alkyl ($C_{1-6}$), lower alkoxy ($C_{1-6}$), cycloalkyl, cycloalkoxy, aryl ($C_{6-12}$), substituted aryl or hydroxy and n is 0, 1, 2, 3, or 4. More preferably, $R_2$ is aryl ($C_{6-12}$) or selected from the group of Formula II, wherein X is selected from Cl, F, or OH. Most preferably, $R_2$ is aryl ($C_{6-12}$) or selected from the group of Formula II, wherein X is Cl.

In a second aspect, the present invention includes a method for the treatment or prevention of hypercholesterolemia comprising the step of administering to a patient a pharmaceutical composition comprising a therapeutically-effective amount of a compound of Formula III:

Formula III

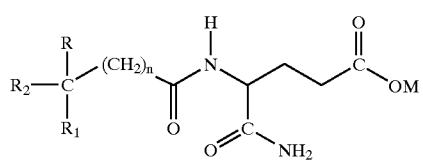

wherein R and $R_1$ are independently selected from the group consisting of H, lower alkoxy ($C_{1-6}$) or lower alkyl ($C_{1-6}$); $R_2$ is selected from the group consisting of aryl ($C_{6-12}$) and substituted aryl; M is hydrogen, sodium, potassium, ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5. Preferably, M is hydrogen or sodium; n is 0; R is selected from the group consisting of H and $C_3H_7$; $R_1$ is selected from the group consisting of H, $CH_3$, $CH_3$—O—, $C_2H_5$, and $C_3H_7$; and $R_2$ is an aryl ($C_{6-12}$) or a substituted aryl selected from the group consisting of Formula II, wherein X is a halogen, lower alkyl ($C_{1-6}$), lower alkoxy ($C_{1-6}$), cycloalkyl, cycloalkoxy, aryl ($C_{6-12}$), substituted aryl or hydroxy and n is 0, 1, 2, 3, or 4. More preferably, $R_2$ is aryl ($C_{6-12}$) or selected from the group of Formula II, wherein X is selected from Cl, F, or OH. Most preferably, $R_2$ is aryl ($C_{6-12}$) or selected from the group of Formula II, wherein X is Cl.

In a third aspect, the present invention includes a method for the treatment or prevention of hypercholesterolemia comprising the step of administering to a patient a pharmaceutical composition comprising a therapeutically-effective amount of a compound of Formula IV:

Formula IV

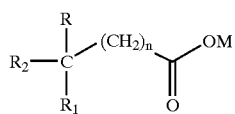

wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, sodium, potassium, ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5. Preferably, M is hydrogen or sodium; n is 0; R is selected from the group consisting of H and $C_3H_7$; $R_1$ is selected from the group consisting of H, $CH_3$, $CH_3$—O—, $C_2H_5$, and $C_3H_7$; and $R_2$ is aryl ($C_{6-12}$) or a substituted aryl selected from the group consisting of Formula II, wherein X is a halogen, lower alkyl ($C_{1-6}$), lower alkoxy ($C_{1-6}$), cycloalkyl, cycloalkoxy, aryl ($C_{6-12}$), substituted aryl or hydroxy and n is 0, 1, 2, 3, or 4. More preferably, $R_2$ is aryl ($C_{6-12}$) or selected from the group of Formula II, wherein X is selected from Cl, F, or OH. Most preferably, $R_2$ is aryl ($C_{6-12}$) or selected from the group of Formula II, wherein X is Cl.

The compositions can optionally include isoglutamine. The compositions can also comprise a pharmaceutically-acceptable carrier, diluent, or excipient. Administration of the compositions can reduce the patient's LDL cholesterol levels. The reduction in the patient's LDL cholesterol levels is expected to reduce the probability of advanced stage atherosclerosis and sequelae such as angina, heart attack, or stroke.

In an additional aspect, the pharmaceutical composition comprises therapeutically-effective amounts of two or more compounds, each compound selected from Formulas I, III, or IV. The compounds can be present in any desired proportion, and the composition can optionally include isoglutamine. The composition can also comprise a pharmaceutically-acceptable carrier, diluent, or excipient. Preferred formulations are a 4:1 ratio of the sodium salts of phenylacetylglutamine and phenylacetylisoglutamine, hereinafter termed "A10," and a 4:1 ratio by mass of sodium phenylacetate to the sodium salt of phenylacetylglutamine, hereinafter termed "AS2-1."

In a further aspect, the invention includes a pharmaceutical composition for the treatment or prevention of hypercholesterolemia, comprising a therapeutically-effective amount of a compound of Formulas I, III, or IV, and optionally isoglutamine and a pharmaceutically-acceptable carrier, diluent, or excipient. Alternatively, the pharmaceutical composition comprises therapeutically-effective amounts of two or more compounds, each compound selected from Formulas I, III, or IV, and optionally isoglutamine and a pharmaceutically-acceptable carrier, diluent, or excipient.

DETAILED DESCRIPTION OF EMBODIMENTS

The invention is described below in terms of preferred embodiments known at the time of filing of this application. These embodiments represent the best mode presently contemplated for preparing the pharmaceutical compositions and their method of use.

A. Preparation of Pharmaceutical Compositions

Pharmaceutical compositions of the present invention comprise a therapeutically-effective amount of a compound of either Formula I:

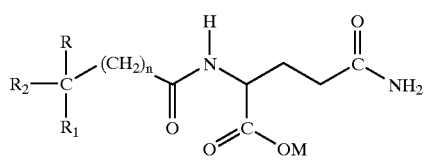

Formula I wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, sodium, potassium, ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5;

Formula III:

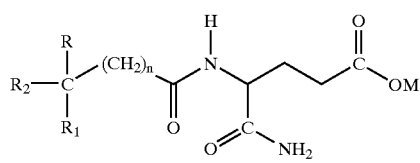

Formula III wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, sodium, potassium, ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5;

or Formula IV:

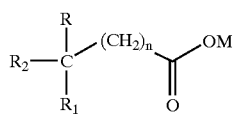

Formula IV wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, sodium, potassium, ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5.

Preferably, in each of Formulas I, III, and IV, M is hydrogen or sodium; n is 0; R is selected from the group consisting of H and $C_3H_7$; $R_1$ is selected from the group consisting of H, $CH_3$, $CH_3$—O—, $C_2H_5$, and $C_3H_7$; and $R_2$ is an aryl ($C_{6-12}$) or a substituted aryl selected from the group consisting of Formula II, wherein X is a halogen, lower alkyl ($C_{1-6}$), lower alkoxy ($C_{1-6}$), cycloalkyl, cycloalkoxy, aryl ($C_{6-12}$), substituted aryl or hydroxy and n is 0, 1, 2, 3, or 4. More preferably, $R_2$ is aryl ($C_{6-12}$) or selected from the group of Formula II, wherein X is selected from Cl, F, or OH. Most preferably, $R_2$ is aryl ($C_{6-12}$) or selected from the group of Formula II, wherein X is Cl.

Preferred compounds are, of Formula I, phenylacetylglutamine, phenylbutylglutamine and sodium salts thereof; of Formula III, phenylacetylisoglutamine, phenylbutylisoglutamine and sodium salts thereof; of Formula IV, phenylacetic acid, phenylbutyric acid and sodium salts thereof.

In another embodiment, the pharmaceutical composition comprises therapeutically-effective amounts of two or more compounds, each compound selected from Formulas I, III, or IV. The compounds can be present in any desired proportion. Preferred formulations of two or more compounds are a 4:1 ratio of the sodium salts of phenylacetylglutamine and phenylacetylisoglutamine, hereinafter termed "A10," and a 4:1 ratio by mass of sodium phenylacetate to the sodium salt of phenylacetylglutamine, hereinafter termed "AS2-1."

Phenylacetylglutamine can be isolated from human body fluids, for example, urine, or it can be synthesized by techniques known in the art, e.g. treatment of phenylacetic acid with N,N'-disuccinimidyl carbonate in acetonitrile followed by reaction with L-glutamine in the presence of $NaHCO_3$ in a 1:1 acetonitrile/water mixture. Phenylacetylglutamine can also be synthesized by the reaction of phenylacetyl chloride with L-glutamine in the presence of $NaHCO_3$ in an aqueous solution. Either D-glutamine or a racemic mixture of glutamine stereoisomers can be used in place of L-glutamine, yielding the corresponding optical isomer of phenylacetylglutamine. Yet another synthesis method that can be used is the treatment of 3-phenylacetylamino-2,6-piperidinedione with sodium hydroxide. Either optical isomer of phenylacetylglutamine, or a mixture thereof in any proportion, can be used in the present invention.

Phenylacetylisoglutamine can be synthesized by the reaction of phenylacetyl chloride with L-glutamine to yield phenylacetylglutamine, with subsequent heating under vacuum at 160° C. to yield 3-phenylacetylamino-2,6-piperidinedione, which can then be treated with sodium hydroxide. Also, phenylacetylisoglutamine can be prepared by treatment of phenylacetic acid with N,N'-disuccinimidyl carbonate in acetonitrile followed by reaction with L-isoglutamine in the presence of $NaHCO_3$ in a 1:1 acetonitrile/water mixture. However, the second synthesis requires L-isoglutamine, which is expensive, so the former route of synthesis is preferred on economic grounds. In either synthetic pathway, D-glutamine or a racemic mixture of glutamine stereoisomers can be used in place of L-glutamine, or D-isoglutamine or a racemic mixture of isoglutamine stereoisomers can be used in place of L-isoglutamine, yielding the corresponding optical isomer of phenylacetylglutamine. Either optical isomer of phenylacetylisoglutamine, or a mixture thereof in any proportion, can be used in the present invention.

Phenylacetic acid can be isolated from human body fluids, for example, urine, or it can be synthesized by techniques known in the art, such as refluxing benzyl cyanide with dilute sulfuric or hydrochloric acid.

Other compounds of Formulas I, III, and IV can be synthesized by techniques known in the art. For example, the acid addition salts may be generated from the free base forms of the compounds by reaction of the latter with one equivalent of a suitable nontoxic, pharmaceutically-acceptable acid, followed by evaporation of the solvent employed for the reaction and recrystallization of the salt, if required. The free base may be recovered from the acid addition salt by a reaction of the salt with a water solution of the salt with a suitable base such as sodium carbonate, sodium hydroxide, and the like.

Suitable acids for forming acid addition salts of the compounds of the present invention include, but are not limited to, acetic, benzoic, benzenesulfonic, tartaric, hydrobromic, hydrochloric, citric, fumaric, gluconic, glucuronic, glutamic, lactic, malic, maleic, methanesulfonic, palmoic, salicylic, stearic, succinic, sulfuric, and tartaric acids. The class of acids suitable for the formation of nontoxic, pharmaceutically-acceptable salts is well known to practitioners of the pharmaceutical formulation arts. (See, for example, Stephen N. Berge, et al. *J. Pharm. Sciences,* 66:1–19 (1977))

The compounds of the present invention may also exist in different stereoisomeric forms by virtue of the presence of one or more asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers in chiral chromotographic columns.

Further, the compounds of the present invention may exist in unsolvated as well as solvated forms with pharmaceutically-acceptable solvents such as water, ethanol, and the like. In general, the solvated forms are considered equivalent to the unsolvated forms for the purposes of the present invention.

Precursors of phenylacetylglutamine, phenylacetylisoglutamine, and phenylacetic acid can be used in the present compositions. Precursors of phenylacetylglutamine, phenylacetylisoglutanine, and phenylacetic acid are hereby defined as compounds that can be metabolized to yield phenylacetylglutamine, phenylacetylisoglutamine, and phenylacetic acid in humans. Pharmaceutically-acceptable precursors of phenylacetylglutamine, phenylacetylisoglutamine, and phenylacetic acid are precursors which lack toxic activity at the selected administration level, either per se or as any metabolic intermediate between the precursor and the final compound. Determination of whether precursors of phenylacetylglutamine, phenylacetylisoglutamine, and phenylacetic acid are pharmaceutically acceptable can be achieved by application of methods known to those of skill in the art. A preferred precursor of phenylacetylglutamine and phenylacetylisoglutamine is 3-phenylacetylamino-2,6-piperidinedione. A preferred precursor of phenylacetic acid for use in the present invention is phenylbutyrate, the structure of which is as follows:

phenylbutyrate

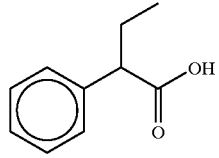

Isoglutamine can optionally be used in the present compositions. Isoglutamine can be extracted from natural body fluids or can be prepared synthetically. For pharmaceutical use, it is preferable that isoglutamine be prepared synthetically. The structural formula of isoglutamine is:

isoglutamine

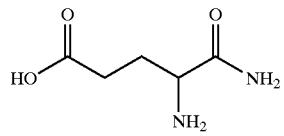

One or more compounds of Formulas I, III, or IV, and optionally isoglutamine, are then combined with an appropriate carrier, diluent, or excipient to prepare a pharmaceutical composition for administration to a patient. The composition should comprise an effective amount of each of the one or more compounds of Formulas I, III, and IV, and optionally isoglutamine, used therein. An "effective amount" of a compound of the present invention is an amount capable of alleviating or preventing hypercholesterolemia when administered by one skilled in the art according to the methods of the present invention. The effective amount of a compound in a pharmaceutical composition of the present invention can be varied depending upon the requirements of the patient, the severity of the condition being treated, and the activity of the compound being employed. The determination of optimum dosages for a particular situation is within the skill of the art.

Typical dosages of the compounds of the present invention are in the range of from about 20 mg/kg/day to 2500 mg/kg/day for human patients. Preferred dosages are in the range of 30 mg/kg/day to 200 mg/kg/day. A typical dosage is about 100 mg/kg/day.

The composition can be prepared for administration via a variety of routes, including oral, sublingual, rectal, transdermal, subcutaneous, intravenous, intramuscular, and intranasal. Preferably, the route of administration is oral, rectal, or intravenous.

Pharmaceutical compositions of the present invention can be prepared using techniques and ingredients known to those skilled in the art, examples of which are given in the following paragraphs. A pharmaceutical composition of the present invention can comprise one or more ingredients, other than phenylacetic acid and related compounds, for use as a carrier, diluent, or excipient.

Ingredients that can be used as carriers, diluents, or excipients in the present invention include, but are not limited to, solvents such as water, alcohol, ether, glycerin, oils, and soaps; ointment bases such as hard, soft, or liquid paraffin; emulsifiers such as lanolin, petrolatum, bentonite, magnesium aluminum silicate, gelatin, acacia, methylcellulose, pectin, tragacanth, sodium lauryl sulfate, benzalkonium chloride, and polyethylene glycol 400 monostearate; aqueous gel formers such as acacia, cellulose, chondrus, gelatin, gelatinized starch, and tragacanth; and paste formers such as glycogelatin, paraffin, and starch.

For solid compositions, ingredients that can be used as carriers, diluents, or excipients include, but are not limited to, encapsulants such as hard gelatin or soft gelatin; diluents such as dextrin, lactose, salt, and starch; lubricants such as liquid paraffin, stearic acid, and talc; coatings such as sucrose syrup, starch suspensions, calcium carbonate, magnesium carbonate, cellulose and cellulose derivatives, including cellulose acetate phthalate; lozenge formers such as sugar, gum, and gelatin; and suppository formers such as theobroma oil.

If the composition is intended for oral administration, it can be formulated as a tablet, capsule, powder, or elixir, among others. Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "formulation" or "preparation" is intended to include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, for example, packeted tablets, capsules, and powders in vials or ampoules. The unit dosage form can also be a capsule, cachet, or tablet itself, or it can be the appropriate number of any of these packaged forms.

If the composition is intended for rectal administration, it can be formulated as a suppository. If the composition is intended for intravenous administration, it can be formulated as an intravenous solution in isotonic saline or water, provided the solution is approximately isotonic to blood and at a similar pH. It will be clear to one skilled in the art that the formulations should be made sterile.

B. Method of Administration of Pharmaceutical Compositions

A pharmaceutical composition of the present invention can be administered via whatever route is appropriate for its formulation described above. If the composition is formulated as a tablet or capsule, 1 to 5 tablets or capsules each containing from 1 mg to 1000 mg of phenylacetic acid or related compound can be administered orally 1 to 8 times per day. If formulated as a powder or elixir, 5 mL to 50 mL of elixir or solvent containing from 1 mg to 1000 mg of phenylacetic acid or related compound can be administered orally 1 to 8 times per day.

If formulated as a suppository, one suppository containing from 1 to 1000 mg of phenylacetic acid or related compound can be administered rectally 1 to 8 times per day.

If formulated as an intravenous solution, 1 mL to 80 mL of solution containing 1 mg to 150 mg of phenylacetic acid or related compound can be administered for a period of from 1 min to 240 min, 1 to 8 times per day.

The duration of the therapeutic regimen may be for only so much time as is required for alleviation of hypercholesterolemia, if phenylacetic acid or related compound is administered for treatment of the condition. Alternatively, if phenylacetic acid or related compound is administered as a prophylactic to prevent the occurrence of hypercholesterolemia, the duration of the therapeutic regimen may be for any length of time recommended by the attending physician.

The following example is included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

Lowering LDL Cholesterol and Triglyceride Levels

A patient had pretreatment serum cholesterol of 231 mg/dL and triglycerides of 275 mg/dL. For approximately seven weeks, the patient received a treatment comprising intravenous infusions of compounds termed A10 (a 1:4 mixture of the sodium salts of phenylacetylisoglutamine and phenylacetylglutamine) and AS2-1 (a 1:4 by mass mixture of the sodium salts of phenylacetylglutamine and phenylacetic acid). Both A10 and AS21 were formulated as solutions in sterile water with concentrations of 80 mg/mL. No other ingredients were used. A10 was administered twice daily for 2 h at a flow rate of 250 mL/h, providing a daily dosage of 0.43 g/kg/day. AS2-1 was administered twice daily for 80 min at a flow rate of 150 mL/h, providing a daily dosage of 0.17 g/kg/day. The patient also suffered from adenocarcinoma of the prostate, lupus erythematosus, post-bypass coronary artery disease, and gout in addition to hypercholesterolemia.

At the completion of treatment, the patient had a cholesterol level of 175 mg/dL (a decrease of 24%) and triglycerides of 113 mg/dL (a decrease of 59%), with no observed side effects other than increases in lactic dehydrogenase, SGOT, and SGPT levels. Also, improvement in the adenocarcinoma of the prostate was observed by MRI of the prostate and pelvis.

All of the compositions and methods disclosed and claimed herein can be made and executed without undue experimentation in light of the present disclosure. While the compositions and methods of this invention have been described in terms of preferred embodiments, it will be apparent to those of skill in the art that variations can be applied to the compositions and methods and in the steps or in the sequence of steps of the method described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for the treatment or inhibition of hypercholesterolemia or hypertriglyceridemia in an affected patient, comprising the step of:
    administering to the patient a composition comprising a therapeutically-effective amount of a compound of either Formula I:

a)

Formula I

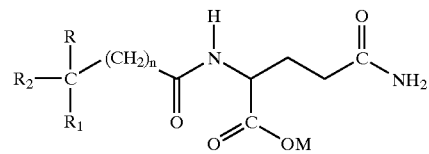

wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, sodium, potassium, ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5; or b) Formula III:

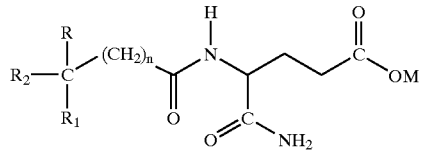

Formula III wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, sodium, potassium, ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5; or c) any combination thereof.

2. The method of claim 1, wherein in said composition M is hydrogen, potassium or sodium; n is 0–2; R and $R_1$ are independently selected from the group consisting of H and $C_3H_7$; $R_1$ is selected from the group consisting of H, $CH_3$, $CH_3$—O—, $C_2H_5$, and $C_3H_7$; and $R_2$ is an aryl ($C_{6-12}$) or a substituted aryl selected from the group consisting of Formula II:

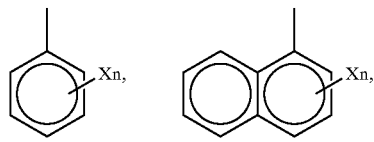

Formula II

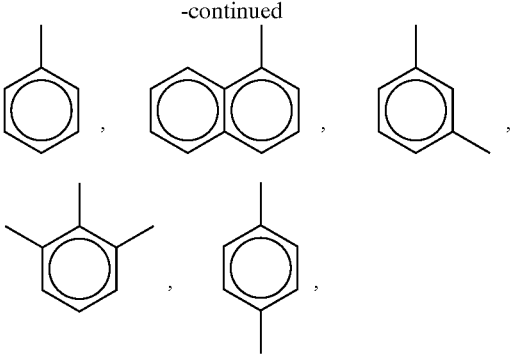

-continued wherein X is a halogen, lower alkyl ($C_{1-6}$), lower alkoxy ($C_{1-6}$), cycloalkyl, cycloalkoxy, aryl ($C_{6-12}$), substituted aryl or hydroxy and n is 0, 1, 2, 3, or 4.

3. The method of claim 2, wherein said therapeutically-effective amount is from 20 mg/kg/day to 2500 mg/kg/day.

4. The method of claim 1, wherein said composition further comprises at least tone pharmaceutically-acceptable carrier, diluent, or excipient.

5. The method of claim 2, wherein said composition further comprises at least one pharmaceutically-active carrier, diluent, or excipient.

6. The method of claim 2, wherein said composition comprises an effective amount of phenylbutylglutamine or isophenylbutylglutamine or pharmaceutically acceptable salts thereof.

7. The method of claim 1, wherein the compound of Formula I is the sodium salt of phenylacetylglutamine and the compound of Formula III is the sodium salt of phenylacetylisoglutamine.

8. The method of claim 1, wherein said therapeutically-effective amount is from 20 mg/kg/day to 2500 mg/kg/day.

\* \* \* \* \*